United States Patent [19]

Barfurth et al.

[11] 3,948,964

[45] Apr. 6, 1976

[54] STABILIZATION OF PARTIALLY HYDROLYZED SILICIC ACID ESTERS

[75] Inventors: Dieter Barfurth, Neiderkassel-Rheidt; Werner Dittrich, Herten; Heinz Nestler, Ranzel, all of Germany

[73] Assignee: Dynamit Nobel Aktiengesellschaft, Cologne, Germany

[22] Filed: Nov. 16, 1973

[21] Appl. No.: 416,567

[30] Foreign Application Priority Data
Dec. 1, 1972   Germany............................ 2258900

[52] U.S. Cl..................... 260/448.8 R; 260/448.2 S
[51] Int. Cl.²......................... C07F 7/04; C07F 7/18
[58] Field of Search................ 260/448.8 R, 448.2 S

[56]         References Cited
        UNITED STATES PATENTS

| | | | |
|---|---|---|---|
| 2,623,019 | 12/1952 | Wilcock.................... | 260/448.2 S X |
| 2,837,482 | 6/1958 | Agens...................... | 260/448.2 S X |
| 2,848,417 | 8/1958 | Armstrong et al........ | 260/448.2 S X |
| 2,922,938 | 1/1960 | Petley...................... | 260/448.2 S X |

*Primary Examiner*—Paul F. Shaver
*Attorney, Agent, or Firm*—Burgess, Dinklage & Sprung

[57]            ABSTRACT

A stabilized hydrolyzed silicic acid ester composition comprising a hydrolyzed silicic acid ester in which is dissolved a stabilizer selected from the group consisting of cyclic ethers, ether alcohols, carboxylic acid esters and ketones.

15 Claims, No Drawings

STABILIZATION OF PARTIALLY HYDROLYZED SILICIC ACID ESTERS

BACKGROUND OF THE INVENTION

1. Field of the Invention

This invention relates to the stabilization of hydrolyzed silicic acid esters. More particularly, this invention relates to a method of lengthening the shelf life of completely or partially hydrolyzed silicic acid esters. This invention further relates to stabilized hydrolyzed silicic acid ester compositions.

2. Discussion of the Prior Art

It is known to use hydrolyzed preparations of silicic acid esters as binding agents for ceramic articles and for zinc dust pigments. In practice, the preparation of these hydrolyzed preparations usually begins with tetraethylorthosilicate or a condensed ethylsilicate having a silicon dioxide content of 40%. The hydrolysis of these starting products is performed by partial or complete reaction of the ester groupings with water, usually using an acid catalyst, such as an aqueous 0.5 to 2% HCl solution, the starting products being diluted with anhydrous solvents such as $C_1$ to $C_3$ alcohols, ketoalcohols with up to 6 carbon atoms, $C_3$ and $C_4$ ketones, or methyl acetate.

The above results in the formation of mostly silanols with free OH groups present partially in the form of chains composed of

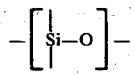

building blocks. In these building blocks, of which an average of 2 to 10 are present per molecule, the free valences of the silicon atom are bound by hydroxyl groups or unreacted alkoxy groups. It is through this hydrolysis that it becomes possible for the silicic acid ester to be used as a binding agent. The binding agents are hardened by drying or the action of hardening accelerators of a usually basic reaction.

Among other uses, these hydrolyzed silicic acid esters serve as binding agents in the preparation of investment molds based on "lost" models. In this process a shell mold of ceramic material is built up by repeatedly coating a model made of wax or plastic or other such material with a suspension of a finely divided refractory material in a hydrolyzed silicic acid ester preparation. After the ceramic shell has hardened the model is removed and the resultant casting mold is fired. It is especially suited for the manufacture of very precise castings having a fine surface.

Hydrolyzed preparations of silicic acid esters are also used in the manufacture of massive divided ceramic casting molds. In this process, the molding composition consists of a refractory material containing even coarser grains, and a silicic acid ester preparation. A hardening agent is added to this molding composition in such quantity that, after the molding composition has been poured over a divided model, it will harden within a set time. After the molding composition has hardened the divided model is removed, and the resultant mold is fired. Castings made in such molds have a smooth surface and are of great accuracy.

When hydrolyzed silicic acid ester preparations are used as binding agents for zinc dust pigments, pigment zinc dust is added to the binding agent in such quantity that there is developed a pigment which can be applied to a sand-blasted iron or steel surface by spraying, brushing or rolling. The coatings made of such pigment are hard and adhere tightly to the substrate and offer lasting protection from corrosion.

The technical advantages which the hydrolysis preparations of silicic acid esters offer are offset by their limited shelf life. During storage, hydrolyzed silicic acid esters are subject to alterations which limit the length of time for which they can be used. These alterations are based upon the fact that the free hydroxyl groups of the silanols are decomposed according to the equation:

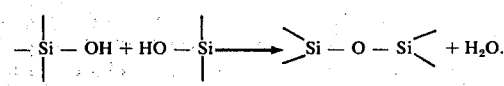

In this process long-chained or branched siloxanes of higher molecular weight averaging more than 10 Si-O units are formed which have very few if any free hydroxyl groups. Such siloxanes therefore no longer have any binding properties and accordingly may no longer be used for the above-described applications. Since this siloxane formation may be considered to be an aging process, one therefore speaks of the "shelf life" of the hydrolyzates. This shelf life is dependent upon several factors, some of which are named herewith:

a. The amount of water used in the hydrolysis,
b. The nature and amount of the catalyst,
c. Temperature during performance of the hydrolysis,
d. Duration of the hydrolysis reaction,
e. Nature and amount of the solvent used,
f. The influence of ultrasound during hydrolysis, and
g. Temperature and atmospheric humidity at which the hydrolyzate is stored.

Heretofore, the lengthening of the shelf life of silicic acid ester hydrolyzates has been possible only by suitably balancing the above factors against one another. Therefore, it has become desirable to provide a means for lengthening the shelf life of such silicic acid ester hydrolyzates which does not involve balancing the above factors against one another. Such a method should be one which can be readily accomplished and which substantially lengthens the shelf life at least about 20%.

SUMMARY OF THE INVENTION

The long felt desires in the art for the lengthening of the shelf life of silicic acid ester hydrolyzates are met, in accordance with this invention, by including in the silicic acid ester hydrolyzate composition in dissolved form a stabilizer of the group consisting of cyclic ethers, ether alcohols, carboxylic acid esters and ketones. Accordingly, the present invention can be considered as a stabilized hydrolyzed silicic acid ester composition comprising a hydrolyzed silicic acid ester and at least one stabilizer dissolved therein of the group consisting of cyclic ethers, ether alcohols, carboxylic acid esters and ketones.

The present invention is directed to the stabilization of all completely or partially hydrolyzed silicic acid esters. Indeed, the use of the stabilizers of the present invention stabilizes all of such hydrolyzed silicic acid esters regardless of the precise chemical composition. When the term "partially hydrolyzed" is used, it refers to a degree of hydrolysis of the ester group of the hydrolyzed silicic acid ester between 10 and 90%, especially from 15% to 30%. The hydrolyzed silicic acid ester can be a simple hydrolyzed silicic acid ester such as one obtained from the hydrolysis of ethylorthosilicate, especially tetraethylorthosilicate, or it can be a silicate which has undergone extensive hydrolysis such as ethylpolysilicate.

By the inclusion of the stabilizers of the present invention in a hydrolyzed silicic acid ester composition, the shelf life can be markedly lengthened without producing any disadvantages. For instance, the shelf life is extended at least 20% and in some instances, the shelf life is doubled, all as will be seen from the data below. This lengthening of the shelf life is provided by including in the hydrolyzed silicic acid ester composition in dissolved form the stabilizers of the present invention. Generally speaking, the stabilizers are included in the hydrolyzed silicic acid ester composition in an amount between 1 and 30% by weight based upon the weight of the stabilized hydrolyzed silicic acid ester composition. Preferably, the stabilizers are included in the composition in an amount between 8 and 12% by weight. It should be understood that other compositions, both active and inactive, can be included in the hydrolyzed silicic acid ester composition. Excellent results are obtained when the stabilizer is present in amounts of about 5%, which amounts provide decided improvements in the shelf life of the silicic acid hydrolyzates. Amounts of about 10% based upon the weight of the overall composition are also particularly useful. It should be understood, however, that these stabilizers are present in the hydrolyzed silicic acid ester preparation in dissolved form.

DESCRIPTION OF PREFERRED EMBODIMENTS

The cyclic ethers employed in accordance with the invention are generally those which are substituted or unsubstituted cycloaliphatic cyclic ethers, especially cyclic ethers having at least 6 atoms in the ring. Examples of such cyclic ethers include 1,4-dioxane, 1,3-dioxane or trioxane. Cyclic ethers with 5 atoms in the ring can also be employed in accordance with the invention, dioxolane being a typical example.

The ether alcohols which are utilized in accordance with the invention are those which have the following formula:

$R^1$-O-$R^2$-OH in which $R^1$ and $R^2$ independently represent substituted or unsubstituted alkyl or alkylene radicals, preferably alkyl or alkylene radicals having up to 6 carbon atoms. Examples of such ether alcohols include methoxybutanol, ethoxybutanol, ethoxyethanol, butoxyethanol, ethoxyhexanol, and isobutoxypentanol.

The carboxylic acid esters that can be used in accordance with the invention include, in particular, the $C_1$ to $C_6$ alkyl esters of $C_1$ to $C_4$ aliphatic carboxylic acids, especially alkanoic acids. The alcohol component of the ester can be capable of being a bivalent alcohol. Examples of such esters of alkanoic acid include ethylacetate, butylacetate, ethylpropionate and ethylglycolacetate.

As ketones, those ketones which can be utilized in accordance with the present invention have chain lengths up to 10 carbon atoms, including the carbon atom of the keto group. Examples of such compounds are methylethylketone, methylisobutylketone, diethylketone, di-n-propylketone and diisobutylketone. The silicic acid esters and their hydrolyzates are those of the type specified above. Preferably, the silicic acid esters are ethyl esters. However, the corresponding hydrolyzates of methyl, propyl, butyl and isobutyl alkyl esters of silicic acid can also be utilized in the binding agent composition stabilized in accordance with the present invention.

The stabilizers of the present invention are added to the hydrolyzed silicic acid ester composition either by combining the stabilizer with the mixture of silicic acid ester, water, catalyst and solvent prior to hydrolysis or by mixing the stabilizer together with the finished hydrolyzate.

In order to more fully illustrate the nature of the invention and the manner of practicing the same the following examples are presented.

In the following examples, the stabilizing effect was tested by comparative experiments at 70°C. The storage life at room temperature (about 22°C) is found by experience to be more than ten times longer than is the storage life at 70°C.

EXAMPLE 1

Several specimens were prepared with various stabilizers in the following manner: to 540 g of an ethyl polysilicate containing 40% $SiO_2$, a mixture of 55 g of 1% aqueous hydrochloric acid, 305 g of ethyl alcohol and 100 g of the stabilizer named in Table 1 is added portion-wise, and the solution obtained was stored at 70°C. A determination was made of the time it took for the solution to gel. Instead of the stabilizer, 100 g of ethanol was added to the blank specimen.

The lengthening of the shelf life is apparent from the following Table 1.

Table 1

| Stabilizer added 100 g | Storage time at 70°C Days |
|---|---|
| Blank specimen | 10 |
| 1,4-dioxane | 24 |
| 4-Methoxybutanol-(1) | 17 |
| 2-Ethoxyethanol-(1) | 13 |
| 2-Butoxyethanol-(1) | 12 |
| Ethyl acetate | 17 |
| Butyl acetate | 17 |
| 2-Ethoxyethyl acetate | 13 |
| Methylethyl ketone | 21 |
| Methylisobutyl ketone | 17 |

EXAMPLE 2

Several hydrolyzed silicic acid ester preparations were prepared by the portion-wise addition of a mixture of 100 g of 1% aqueous hydrochloric acid and 134 g of ethyl alcohol to 666 g of tetraethylorthosilicate. 100 g of the stabilizers named in Table 2 were added to each of the preparations. The blank specimen additionally received, instead of the stabilizer, the same amount of ethyl alcohol.

The length of time it took for gelation to occur during storage at 70°C was determined. The results appear in Table 2.

Table 2

| Stabilizer added 100 g | Storage time at 70°C Days |
|---|---|
| Blank specimen | 13 |
| 1,4-dioxane | 40 |
| 4-Methoxybutanol-(1) | 38 |
| 2-Ethoxyethanol-(1) | 26 |
| 2-Butoxyethanol-(1) | 21 |
| Ethyl acetate | 33 |
| Butyl acetate | 32 |
| 2-Ethoxyethyl acetate | 28 |

Table 2-continued

| Stabilizer added 100 g | Storage time at 70°C Days |
|---|---|
| Methylethyl ketone | 39 |
| Methylisobutyl ketone | 31 |

What is claimed is:

1. A stabilized silicic acid ester composition comprising a partially hydrolyzed silicic acid ester having between 2 and 10-[Si-O]- groups and, dissolved therein, a stabilizer selected from the group consisted of cyclic ethers containing carbon, hydrogen and oxygen only, ether alcohols having the formula $R^1$-O-$R^2$-OH in which $R^1$ and $R^2$ independently represent alkyl or alkylene radicals having up to 6 carbon atoms, carboxylic acid alkyl esters wherein the alkyl group has 1 to 6 carbon atoms, the carboxylic acid being in dissolved form, and ketones having a chain length of up to 10 carbon atoms.

2. A composition according to claim 1 wherein the stabilizer is present in an amount of from 1 to 30% by weight, based upon the weight of the entire composition.

3. A composition according to claim 2 wherein the stabilizer is present in an amount between 8 and 12% by weight, based upon the weight of the entire composition.

4. A hydrolyzed silicic acid ester composition consisting essentially of a partially hydrolyzed silicic acid ester and, dissolved therein, a stabilizer selected from the group consisting of cyclic ethers containing carbon, hydrogen and oxygen only, ether alcohols having the formula $R^1$-O-$R^2$-OH wherein $R^1$ and $R^2$ are each independently alkyl or alkylene radicals having up to 6 carbon atoms, carboxylic acid alkyl esters wherein the alkyl portion has 1 to 6 carbon atoms and ketones having up to 10 carbon atoms in the chain.

5. A composition according to claim 4 wherein the stabilizer is a cyclic ether having at least 5 atoms in the ring.

6. A composition according to claim 5 wherein the cyclic ether has at least 6 atoms in the ring.

7. A composition according to claim 6 wherein the cyclic ether is selected from the group consisting of 1,4-dioxane, 1,3-dioxane, trioxane and dioxolane.

8. A composition according to claim 5 wherein the cyclic ether is present in an amount between 1 and 30% by weight, based upon the weight of the entire composition.

9. A composition according to claim 4 wherein the stabilizer is an ether alcohol and the ether alcohol is present in an amount of 1 to 30%, based upon the weight of the entire composition.

10. A composition according to claim 9 wherein the ether alcohol is selected from the group consisting of 2-methoxybutanol-(1), 2-ethoxyethanol-(1), 4-ethoxybutanol-(1), 2-butoxyethanol-(1), 6-ethoxyhexanol-(1) and 5-isobutoxypentanol-(1).

11. A composition according to claim 4 wherein the stabilizer is a carboxylic acid ester wherein the acid is a $C_1$ to $C_4$ aliphatic carboxylic acid, said carboxylic acid ester being present in an amount from 1 to 30% by weight, based upon the weight of the entire composition.

12. A composition according to claim 11 wherein the carboxylic acid ester is selected from the group consisting of ethylacetate, butylacetate, ethylpropionate and 2-ethoxyethylacetate.

13. A composition according to claim 4 wherein the stabilizer is a ketone and the ketone is present in an amount from 1 to 30% by weight, based upon the weight of the entire composition.

14. A composition according to claim 13 wherein the ketone is selected from the group consisting of methylethyl ketone, methylisobutyl ketone, diethyl ketone, di-n-propyl ketone and diisobutyl ketone.

15. A composition according to claim 4 wherein the stabilizer is present in an amount from 8 to 12% by weight, based upon the weight of the entire composition.

* * * * *